US00PP13010P2

(12) United States Plant Patent
van Tol

(10) Patent No.: US PP13,010 P2
(45) Date of Patent: Sep. 24, 2002

(54) DELPHINIUM PLANT NAMED 'DOLCE VITA'

(75) Inventor: Benjamin Roelof van Tol, Abbenes (NL)

(73) Assignee: Witteman + Co. 'Multiflora' B.V., Hillegom (NL)

( * ) Notice: Subject to any disclaimer, the term of this patent is extended or adjusted under 35 U.S.C. 154(b) by 2 days.

(21) Appl. No.: 09/838,942

(22) Filed: Apr. 23, 2001

(51) Int. Cl.[7] ..... A01H 5/00
(52) U.S. Cl. ..... Plt./263

(58) Field of Search ..... Plt./263

(56) References Cited

PUBLICATIONS

UPOVE ROM GTITM Computer Database, 2001/06, GTI JOUVE Retrieval Software, citation for 'Dolce Vita'.

*Primary Examiner*—Bruce R. Campell
*Assistant Examiner*—W C Baker
(74) *Attorney, Agent, or Firm*—C. A. Whealy

(57) ABSTRACT

A distinct cultivar of Delphinium plant named 'Dolce Vita', characterized by its upright plant habit; freely flowering habit; and double violet and blue bi-color flowers.

2 Drawing Sheets

BOTANICAL CLASSIFICATION

*Delphinium elatum.*

BACKGROUND OF THE INVENTION

The present Invention relates to a new and distinct cultivar of Delphinium plant, botanically known as *Delphinium elatum*, and hereinafter referred to by the name 'Dolce Vita'.

The new Delphinium was discovered by the Inventor in a controlled environment in Abbenes, The Netherlands, as a naturally- occurring mutation of an unidentified selection of *Delphinium elatum*. The new Delphinium was slected by the Inventor on the basis of its double violet and blue bi-colored flowers.

Asexual reproduction of the new cultivar by cuttings in a controlled environment in Hillegom, The Netherlands, since 1999, has shown that the unique features of this new Delphinium are stable and reproduced true to type in successive generations.

SUMMARY OF THE INVENTION

Plants of the cultivar Dolce Vita have not been observed under all possible environmental conditions. The phenotype may vary somewhat with variations in environment such as temperature, light intensity, daylength, irrigation amount and frequency, and/or fertilizer type or rate without, however, any variance in genotype.

The following traits have been repeatedly observed and are determined to be the unique characteristics of 'Dolce Vita'. These characteristics in combination distinguish 'Dolce Vita' as a new and distinct cultivar:

1. Upright plant habit.
2. Freely flowering habit.
3. Double violet and blue bi-colored flowers.

Plants of the cultivar Dolce Vita differ from the parent selection and other known cultivars of Delphinium in its double flower form and flower color.

BRIEF DESCRIPTION OF THE PHOTOGRAPHS

The accompanying colored photographs illustrate the overall appearance of the new Delphinium, showing the colors as true as it is reasonably possible to obtain in colored reproductions of this type. Colors in the photographs may differ slightly from the color values cited in the detailed botanical description which accurately describe the colors of the new Delphinium.

The photograph on the first sheet comprises a side perspective view of a typical flowering plant of 'Dolce Vita'. The photograph at the top of the second sheet is a close-up view of typical flowers of 'Dolce Vita'.

The photograph at the bottom of the second sheet is a close-up view of the upper surface of a typical leaf of 'Dolce Vita'.

DETAILED BOTANICAL DESCRIPTION

In the following description, color references are made to The Royal Horticultural Society Colour Chart except where general terms of ordinary dictionary significance are used. Plants used for the photographs and the following description were about 6 months old and grown under field conditions which closely approximate commerical production conditions during the spring and summer in Hillegom, The Netherlands.

Botanical classification: *Delphinium elatum* cultivar Dolce Vita.

Parentage: Naturally-occurring mutation of an unidentified selection of *Delphinium elatum*, not patented.

Propagation:

*Type cutting.*—By cuttings.

*Time to initiate roots.*—About 14 days at 14° C.

*Time to produce a rooted cutting.*—About 40 days at 20° C.

*Root description.*—Fine.

Plant description:

*Form.*—Upright perennial flowering plant with double flowers arranged on erect racemes. During a growing season, about eight flower racemes develop per plant.

*Crop time*.—After rooting, about 6 months are required to produce finished flowering plants in 2-liter containers.

*Plant height*.—About 100 cm.

*Plant diameter*.—About 40 cm.

*Vigor*.—Moderately vigorous to vigorous.

*Flowering stems*.—Length: About 50 cm. Diameter: About 4 mm. Internode length: About 3 cm. Texture: Smooth, slightly glaucous. Color: 138B to 139C.

*Foliage description*.—Leaves simple, generally symmetrical, and long-persisting. Arrangement: Rosette at the base and alternate along flowering stems. Length: About 18 cm. Width: About 25 cm. Shape: Deeply palmately to pedately-lobed. Apex: Acute. Base: Attenuate. Margin: Incised. Texture: Upper surface: Glabrous. Lower surface: Sparsely pubescent at margins. Venation pattern: Laciniate. Color: Young foliage, upper surface: 137A. Young foliage, lower surface: 137C to 137D. Fully expanded foliage, upper surface: 137A to 141A; venation, 137A to 141A. Fully expanded foliage, lower surface: 137C to 138A; venation, 144A. Petiole: Length: About 11 cm. Diameter: About 3 by 5 mm. Texture: Smooth. Color: 144A.

Flower description:

*Appearance*.—Numerous, double flowers arranged in racemes; zygomorphic. Flowers not persistent.

*Quantity of flowers*.—Freely flowering. Primary or main flowering stem, about 60 flowers; secondary flowering stems, about 20 flowers each.

*Natural flowering season*.—Late summer in The Netherlands; flowering continuous during this period.

*Fragrance*.—Slightly fragrant, typical of Delphinium.

*Flower longevity on the plant*.—About 10 to 14 days.

*Flower longevity as a cut flower*.—At least 10 days.

*Flower size*.—Diameter: About 6 cm. Depth, excluding spur: About 2.2 cm.

*Flower buds*.—Length, excluding spur: About 1.8 cm. Diameter: About 1.5 cm. Shape: Ovoid to orbicular. Color: 115D.

*Petals/petaloids*.—Appearance/arrangement: About 5 petals and about 17 petaloids per flower arranged in multiple whorls. Length: Petals: About 3 cm. Petaloids, largest: About 3 cm. Width: Petals: About 2.5 cm. Petaloids, largest: About 2.5 cm. Shape: Petals: Broadly elliptic. Petaloids: Outer petaloids: Broadly elliptic. Innermost petaloids: Spatulate to flabellate. Apex: Abruptly acute. Margin: Entire. Texture: Smooth, slightly rugose. Color: Petals: When opening, upper surface: Margin, 100B to 101B; center and base, 84C. When opening, lower surface: 100C to 101C, with a green, 141B to 141C, spot towards the petal apex. Fully opened, upper surface: 101B. Fully opened, lower surface: 101C, with a green, 141B, spot towards the apex. Petaloids: Immature, both surfaces: Margins, 104B; center and base, 75A to 76A; random white, 155D, areas towards the apex. Mature, both surfaces: Margins, 101B to 104B; center and base, 76A; random white, 155D, areas towards the apex. Spur: Arrangement: On uppermost outer petal, downwardly bending. Length: About 2 cm. Diameter: About 1 mm. Color: 138B to 138C.

*Sepals*.—Appearance/arrangement: Two per flower; opposite. Calyx length: About 1.4 cm. Calyx diameter: About 1.4 cm. Shape: Linear. Apex: Acuminate. Margin: Entire. Texture: Sparsely pubescent. Color, both surfaces: 141A to 141B.

*Pedicel*.—Length: About 6 cm. Angle: About 30° from vertical. Strength: Strong. Texture: Smooth. Color: 141B.

*Reproductive organs*.—Stamens: Quantity: About 25 per flower. Anther length: About 1 mm. Anther shape: Reniform. Anther color: 200B. Pollen amount: Scarce. Color: Pale creamy white, close to 158A. Pistils: Quantity: Six per flower. Pistil length: About 3 mm. Stigma shape: Two-parted. Stigma color: Close to 155D. Style length: About 3 mm. Style color: Close to 155D. Ovary color: 143B.

*Seed description*.—Shape: Roughly spherical. Length: About 1.5 mm. Diameter: About 1.5 mm. Color: 200A to 202A.

Disease resistance: Plants of the new Delphinium have not been noted to be resistant to pathogens common to Delphinium.

It is claimed:

1. A new and distinct cultivar of Delphinium plant named 'Dolce Vita', as illustrated and described.

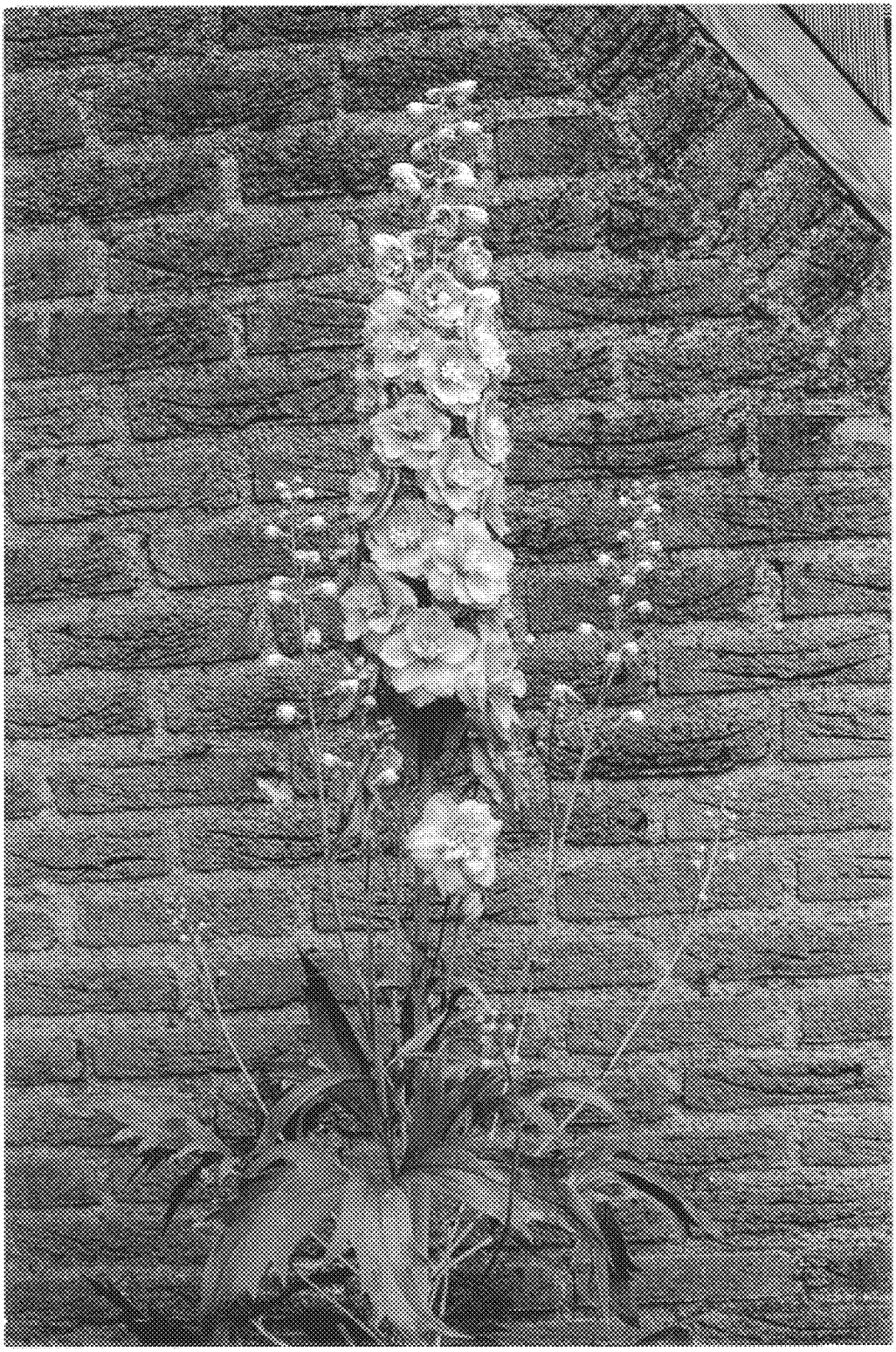

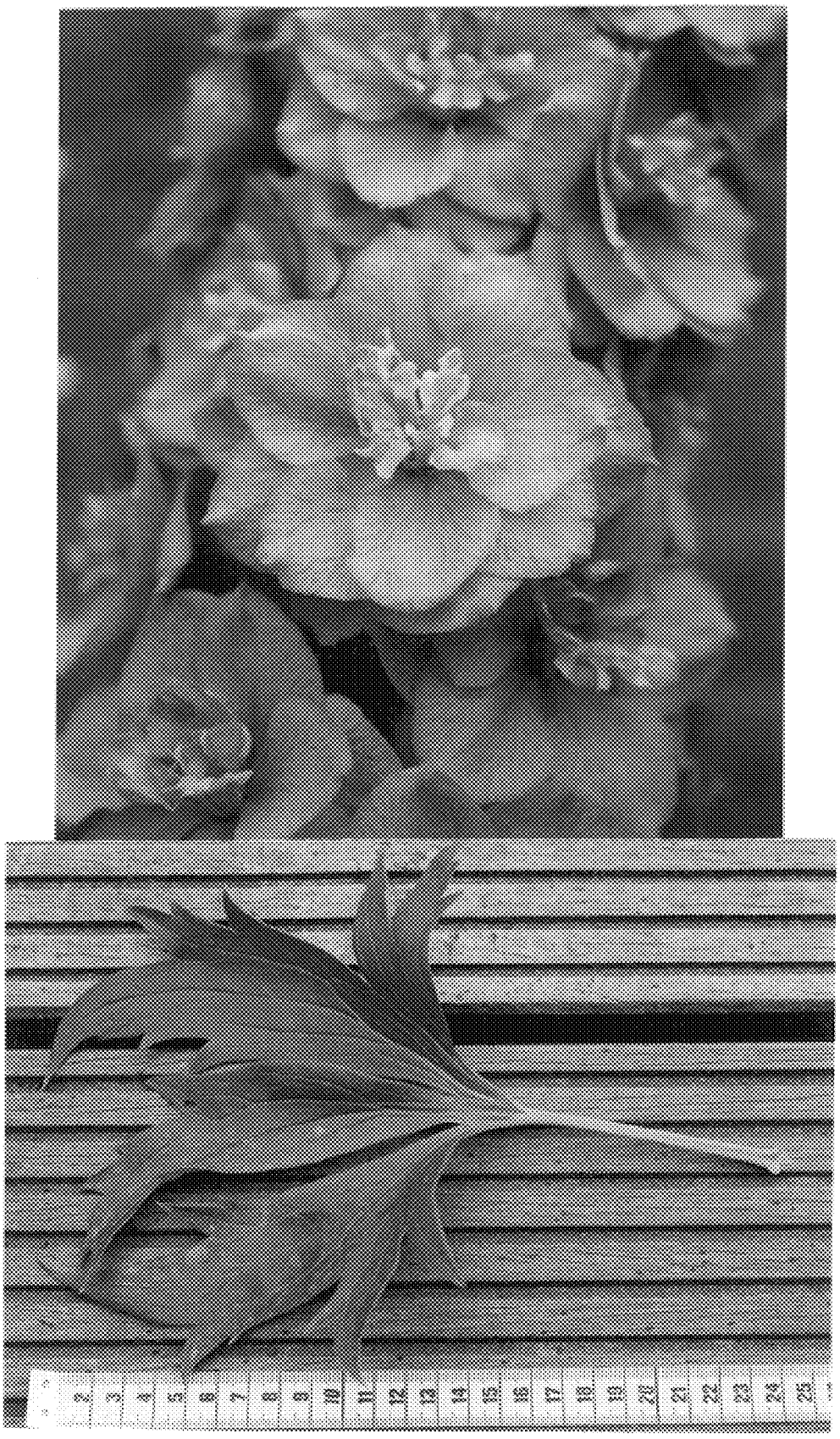

* * * * *